United States Patent [19]

Henrick

[11] B 3,981,922

[45] Sept. 21, 1976

[54] DI-OLEFINIC KETONES

[75] Inventor: Clive A. Henrick, Palo Alto, Calif.

[73] Assignee: Zoecon Corporation, Palo Alto, Calif.

[22] Filed: May 9, 1974

[21] Appl. No.: 468,350

[44] Published under the second Trial Voluntary Protest Program on January 13, 1976 as document No. B 468,350.

Related U.S. Application Data

[63] Continuation-in-part of Ser. No. 201,167, Nov. 22, 1971, abandoned, which is a continuation-in-part of Ser. No. 187,898, Oct. 8, 1971, Pat. No. 3,752,843, which is a continuation-in-part of Ser. No. 111,701, Feb. 1, 1971, abandoned.

[52] U.S. Cl. .......................................... 260/593 R
[51] Int. Cl.$^2$ ........................................ C07C 49/20
[58] Field of Search ................. 260/593 R, DIG. 44

[56] References Cited

UNITED STATES PATENTS

| | | | |
|---|---|---|---|
| 3,712,922 | 1/1973 | Henrick et al. | 260/593 R |
| 3,729,486 | 4/1973 | Siddall | 260/DIG. 44 |
| 3,816,484 | 6/1974 | Henrick | 260/593 R |

OTHER PUBLICATIONS

Slama et al., Proceeding of the National Academy of Science, Vol. 54, pp. 411–414, (1965).
Sarmiento et al., Science, Vol. 179, pp. 1342–1343.

*Primary Examiner*—James O. Thomas, Jr.
*Assistant Examiner*—James H. Reamer
*Attorney, Agent, or Firm*—Donald W. Erickson

[57] ABSTRACT

Aliphatic hydrocarbon di-olefinic ketones prepared by the reaction of a di-olefinic acid with organo-lithium which are useful for the control of insects.

3 Claims, No Drawings

DI-OLEFINIC KETONES

This application is a continuation-in-part of application Ser. No. 201,167, filed Nov. 22, 1971 now abandoned which is, in turn, a continuation-in-part of application Ser. No. 187,898, filed Oct. 8, 1971, now U.S. Pat. No. 3,752,843, which is, in turn, a continuation-in-part of application Ser. No. 111,701, filed Feb. 1, 1971, now abandoned, the disclosures of which are incorporated by reference.

This invention relates to novel aliphatic olefinic compounds, intermediates therefor, synthesis thereof and the control of insects. More particularly, novel olefinic compounds of the present invention are represented by the following formula (A):

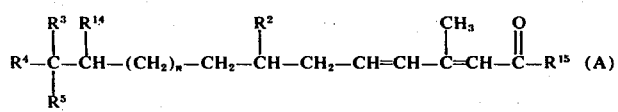

wherein,
$n$ is zero or one;
each of $R^2$ and $R^3$ is methyl or ethyl;
each of $R^4$ and $R^{15}$ is lower alkyl;
$R^5$ is hydrogen, methyl or ethyl; and
$R^{14}$ is hydrogen or methyl.

The compounds of formula A are useful for the control of insects. The utility of these compounds as insect control agents is believed to be attributable to their juvenile hormone activity. They are preferably applied to the immature insect, namely - during the embryo, larvae or pupae stage in view of their effect on metamorphosis and otherwise cause abnormal development leading to death or inability to reproduce. These compounds are effective control agents for Hemipteran such as Lygaeidae, Miridae and Pyrrhocoridae; Lepidopteran such as Pyralidae, Noctuidae and Gelechiidae; Coleopteran such as Tenebrionidae, Crysomelidae and Dermestidae; Dipteran such as mosquitos, flies, Homopteran such as aphids and other insects. The compounds can be applied at low dosage levels of the order of 0.001 µg. to 25.0 µg. per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of the compounds of formula A. Generally, a concentration of less than 25% of the active compound is employed. The formulations can include insect attractants, emulsifying agents or wetting agents to assist in the application and effectiveness of the active ingredient. In the application of the compounds, there is generally employed a mixture of the $\alpha,\beta$ trans and cis isomers. Mixtures containing predominantly the $\alpha,\beta$-trans isomer are preferred.

In the description hereinafter, each of $R^2$–$R^5$, $R^{14}$–$R^{15}$, and $n$ is as defined hereinabove unless otherwise specified.

The ketones of formula A can be prepared by treatment of an ester of or an acid of formula B with the appropriate organolithium, the organo group corresponding to the ketone moiety desired. The reaction is generally carried out in an organic solvent such as an ether solvent. In addition, acid halides of formula B, particularly the acid chloride, can be used for the preparation of ketones of formula A by reaction with lithium diorganocopper, e.g. lithium dimethylcopper, using the procedure of Posner and Whitten, *Tetrahedron Letters*, No. 53, 4647 (1970).

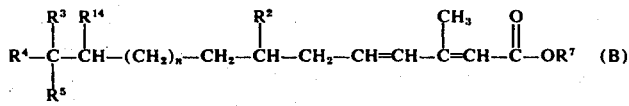

wherein $R^7$ is hydrogen or lower alkyl.

The synthesis of esters and acids of formula B and acid halides thereof is fully described in application Ser. No. 187,898 filed Oct. 8, 1971, now U.S. Pat. No. 3,752,843. The synthesis can be outlined as follows:

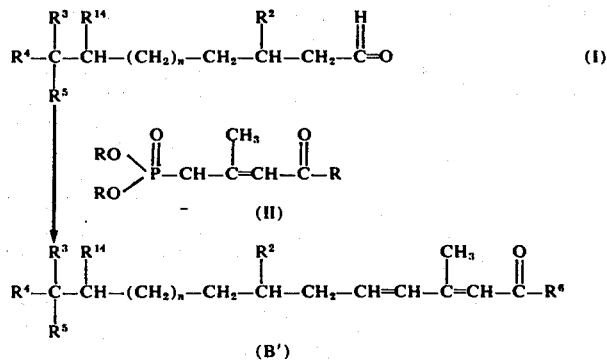

In the above formulas, R is lower alkyl and $R^6$ is lower alkoxy.

In the above synthesis, an aldehyde of formula I is reacted with a carbanion of formula II to yield an ester of formula B′.

The carbanion (II) is generated by treatment of the corresponding phosphonate with a base such as an alkali hydroxide, alkali hydride or alkali alkoxide, e.g.

NaOH, NaH, sodium ethoxide or sodium methoxide, in an organic solvent inert to the reaction such as hydrocarbon, ether or dialkylsulfoxide solvent e.g. benzene, toluene, dimethylformamide or tetrahydrofuran. The reaction is generally conducted at a temperature of from about −20°C to room temperature or above. The reaction of the carbanion with the carbonyl (I) is generally conducted at temperature of about 0°C to room temperature or above. The phosphonates can be prepared as described by Pattenden and Weedon J. Chem. Soc. (C), 1984 and 1997 (1968), Stilz and Pommer, U.S. Pat. Nos. 3,163,669 and 3,177,226 and Corey et al., Tetrahedron Letters No. 2, 1821 (1971).

The esters of B' are converted into the corresponding acid by hydrolysis with base such as potassium carbonate, sodium carbonate, sodium hydroxide, and the like in organic solvent such as methanol or ethanol. The acid can be converted into the acid halide by treatment with thionyl chloride, oxalyl chloride, phosphorous pentabromide or the like.

The term "lower alkyl" refers to an alkyl group having a chain length of one to six carbon atoms.

In addition to the compounds of the present invention having activity useful for the control of insects, the compounds of formula A are useful in perfumery compositions in view of their odor-imparting properties.

The presence of $\alpha,\beta$ and $\gamma,\delta$ olefinic bonds, with respect to the carbonyl portion of the molecule gives rise to four isomers, each of which is embraced by the present invention. As mentioned above, a mixture of isomers is suitably employed for the control of insects such as a mixture containing the trans $\alpha,\beta$, trans $\gamma,\delta$ isomer and the cis $\alpha,\beta$, trans $\gamma,\delta$ isomer. The conditions of the syntheses described herein and the reactants can be selected so as to favor formation of one isomer such as the all trans isomer over the formation of other isomers. The selection of appropriate conditions and reactants to favor formation of one isomer over another will be apparent to those of ordinary skill in the art giving due consideration to the specific examples hereinafter. See also Pattenden and Weedon, supra and Corey et al., supra. In the specific examples hereinafter, when isomerism is not specified, it is understood to include a mixture of isomers which, if desired, can be separated using known separation methods. Hereafter, when only one designation of configuration is given, the designation refers to the $\alpha,\beta$- position and the configuration is taken to be trans at the $\gamma,\delta$ position when not otherwise specified. The use of "trans/cis" and "cis/trans" is with reference to the $\alpha,\beta$- position and indicates a mixture of isomers.

The following examples are provided to illustrate the practice of the present invention. Temperature is given in degrees Centigrade.

EXAMPLE 1

To a stirred solution of 2.5 g. of 3,7,11,11-tetramethyltrideca-2,4-dienoic acid in 30 ml. of dry ether is added slowly, at 0°, 23 ml. of a one molar solution of ethyl lithium in benzene. After about three hours at 20°, the mixture is poured into iced 1N hydrochloric acid (100 ml.) with vigorous stirring. The ether layer is separated, combined with ethereal washings of the aqueous phase, washed with water, saturated potassium bicarbonate, and then saturated brine, dried over magnesium sulfate and concentrated under reduced pressure to yield 5,9,13,13-tetramethylpentadeca-4,6-dien-3-one which is purified by high vacuum distillation or chromatography.

By using methyl lithium, in the foregoing procedure in place of ethyl lithium, there is obtained 4,8,12,12-tetramethyltetradeca-3,5-dien-2-one.

EXAMPLE 2

The process of Example 1 is repeated using each of the acids under col. I as the starting material with ethyl lithium to prepare the respective ketone under col. II.

I 3,7,11-trimethyldodeca-2,4-dienoic acid
3,7,11-trimethyltrideca-2,4-dienoic acid
3,11-dimethyl-7-ethyltrideca-2,4-dienoic acid
3,7,10-trimethylundeca-2,4-dienoic acid

II 5,8,13-trimethyltetradeca-4,6-dien-3-one
5,9,13-trimethylpentadeca-4,6-dien-3-one
5,13-dimethyl-9-ethylpentadeca-4,6-dien-3-one
5,9,12-trimethyltrideca-4,6-dien-3-one Methyl lithium is reacted with each of the acids under col. I to prepare the respective methyl ketone listed below:

4,8,12-trimethyltrideca-3,5-dien-2-one
4,8,12-trimethyltetradeca-3,5-dien-2-one
4,12-dimethyl-8-ethyltetradeca-3,5-dien-2-one
4,8,11-trimethyldodeca-3,5-dien-2-one

EXAMPLE 3

Isopropyl lithium is reacted with each of 3,7,11-trimethyldodeca-2,4-dienoic acid, 3,7,11-trimethyltrideca-2,4-dienoic acid, 3,7,11,11-tetramethyltrideca-2,4-dienoic acid, 3,7,10,11-tetramethyldodeca-2,4-dienoic acid, 3,7,9,10-tetramethylundeca-2,4-dienoic acid, and 3,7,10-trimethylundeca-2,4-dienoic acid, to prepare the respective isopropyl ketone listed below:

2,5,9,13-tetramethyltetradeca-4,6-dien-3-one
2,5,9,13-tetramethylpentadeca-4,6-dien-3-one
2,5,9,13,13-pentamethylpentadeca-4,6-dien-3-one
2,5,9,12,13-pentamethyltetradeca-4,6-dien-3-one
2,5,9,11,12-pentamethyltrideca-4,6-dien-3-one
2,5,9,12-tetramethyltrideca-4,6-dien-3-one

EXAMPLE 4

To 350 ml. of ethanol, 105 ml. of water and 70 ml. of 50% aqueous sodium hydroxide is added 46.5 g. of ethyl 3,7,11-trimethyldodeca-2,4-dienoate (40% cis, trans and 60% trans, trans). The mixture is refluxed for about 19 hours. After cooling, ethanol is removed under reduced pressure and water added followed by extraction with ether to yield 3,7,11-trimethyldodeca-2,4-dienoic acid containing about 58% trans, trans isomer. Conversion of the thus-obtained acid to the S-benzyl-isothiouronium salt recrystallized from aqueous methanol, and regeneration of the acid with ether-aqueous hydrochloric acid provides crystalline trans, trans, 3,7,11-trimethyldodeca-2,4-dienoic acid.

EXAMPLE 5

To a solution of 3.00 g. of trans/cis 3,7,11-trimethyldodeca-2,4-dienoic acid in 50 ml. ether at 0° under nitrogen is added 28.00 ml. of 0.9 M solution of ethyllithium in benzene. The solution is stirred for ½ hour at 0° and then overnight at room temperature. To the reaction mixture is added 50 ml. of ether and the resultant solution is added dropwise with stirring to 300 ml. saturated aqueous ammonium chloride. The organic layer is separated and is washed in turn with 50 ml. saturated aqueous ammonium chloride, 35 ml. water, and 35 ml. saturated aqueous sodium chloride. The solution is dried over calcium sulfate, is concentrated and is then purified by preparative thin layer chromatography (1:3 ether/hexane) and short path distillation (boiling point 100° at .18 mm.) to give 5,9,13-trimethyltetradeca-4,6-dien-3-one (85.4% trans-4, trans-6; 14.6% cis-4, trans-6.).

EXAMPLE 6

To a stirred solution of 9.5 ml. of a one molar solution of ethyllithium in benzene and 50 ml ether, under nitrogen is added at 0° 1.0 g. of 3,7,11,11-tetramethyl-dodeca-2,4-dienoic acid in 10 ml. ether. The reaction mixture is stirred for three hours and then is poured into a rapidly stirred saturated aqueous ammonium chloride solution followed by the addition of 50 ml. of ether. The organic layer is separated and then is washed with saturated sodium chloride. The solution is dried over magnesium sulfate and the solvent is removed to yield 5,9,13,13-tetramethyltetradeca-4,6-dien-3-one.

Although not intending to be limited by a theoretical explanation, the effectiveness of the compounds of the present invention to control insects is attributed to the property of these novel compounds to mimic the activity of juvenile hormone as demonstrated herein. While the methods of applying and carriers for conventional insecticides are usually adaptable to the practical use of the compounds of the present invention, the mechanism of action of these novel compounds is unlike that of conventional insecticides. Whereas conventional insecticides are dependent upon direct knockdown effect, toxity effect or paralyzing effect; the compounds of this invention achieve control by reason of their ability to inhibit metamorphosis, inhibit reproduction due to abnormal development, break diapause at an unfavorable time, or act as a direct insecticide, particularly at the embryo stage and larvae stage. Treatment of insects in accordance with the present invention can be achieved via ingestion of the active compound in the normal food of the insect and by topical application that is by contact of the epidermis of the insect as by spraying the insect and habitat of the insect or exposure to vapors of the active compound which penetrate into the insect.

The compounds of the present invention can be used in conjunction with other juvenile hormone active substances and conventional insecticides to obtain a broader spectrum of activity or to provide more immediate effects on very heterogeneous populations. Typical insecticides which may be combined with the compounds of the present invention are Malathion, Sevin, Vapona, synthetic and natural pyrethrins, and the like and usually within the ratio of between 10:1 and 1:10 by weight.

Galleria mellonella pupae, less than 24 hours old, maintained as larvae at 31°C room temperature, humidity of about 70% and photo-period of 16 hours, are treated topically with the compounds of Table 1 at dosage rates of 0.01, 0.1, 1 and 10 micrograms of compound using acetone as the carrier. Compound 3 is also tested at 100 micrograms. Two groups of ten specimens each are treated at each dosage level with an additional group of ten specimens treated only with acetone as a control. Using a syringe, the test solution is applied topically on that ventral portion of the pupae where the wings meet over the abdomen. Scoring is done when all adults have emerged in the controls, usually ten days after treatment, by determining the percentage of Galleria showing morphogenetic aberrations. The $ID_{50}$ (dosage rate causing morphogenetic aberration in 50% of the specimens) is computed by plotting on semi-logarithmic paper, the dose on the horizontal axis and the percentage response on the vertical axis.

The preparation of Compound 3, is found in U.S. Pat. No. 3,692,851, issued Sept. 19, 1972.

The results of this testing are presented in Table 1 below:

TABLE 1

| Compound | ID-50, μg |
|---|---|
| 1. 5,9,13-trimethyltetradeca-4,6-dien-3-one (85.4% trans-4, trans-6; 14.6% cis-4, trans-6) | 0.070 |
| 2. 5,9,13,13-tetramethyltetradeca-4,6-dien-3-one (87% trans-4, trans-6; 13% cis-4, trans-6) | 0.500 |
| 3. 5,9,9,13,13-pentamethyltetradeca-4,6-dien-3-one (85% trans-4, trans-6; 15% cis-4, trans-6) | >100.0[1] |

[1]The symbol > means "greater than"

What is claimed is:
1. A compound of the formula:

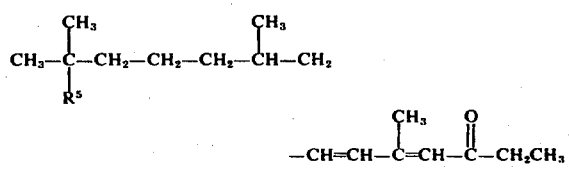

in which $R^5$ is hydrogen or methyl.

2. The compound, 5,9,13-trimethyltetradeca-4,6-dien-3-one, according to claim 1.

3. The trans,trans isomer of the compound of claim 2.

* * * * *